United States Patent [19]
Overton

[11] Patent Number: 6,068,684
[45] Date of Patent: May 30, 2000

[54] MICROSTRUCTURE CHROMATOGRAPH WITH RECTANGULAR COLUMN

[75] Inventor: Edward B. Overton, Baton Rouge, La.

[73] Assignee: Board of Supervisors of Louisiana State University and Agricultural & Mechanical College, Baton Rouge, La.

[21] Appl. No.: 08/927,168

[22] Filed: Sep. 11, 1997

[51] Int. Cl.[7] .................................................. B01D 15/08
[52] U.S. Cl. .............................. 96/104; 96/105; 96/107; 210/656; 210/198.2
[58] Field of Search .................................. 210/656, 659, 210/198.2; 96/101, 104, 105, 107

[56] References Cited

U.S. PATENT DOCUMENTS

| | | | |
|---|---|---|---|
| 3,097,518 | 7/1963 | Taylor et al. | 73/23 |
| 3,150,517 | 9/1964 | Kuffer et al. | 73/23.1 |
| 3,174,326 | 3/1965 | Carle et al. | 73/23.1 |
| 3,503,712 | 3/1970 | Sussman | 23/252 |
| 3,662,520 | 5/1972 | Saunders | 55/158 |
| 3,668,834 | 6/1972 | Deans | 55/67 |
| 3,748,833 | 7/1973 | Karas et al. | 55/197 |
| 4,604,198 | 8/1986 | Dailey | 210/198.2 |
| 4,908,112 | 3/1990 | Pace | 210/198.2 |
| 4,935,040 | 6/1990 | Goedert | 15/8 |
| 5,116,495 | 5/1992 | Prohaska | 210/198.2 |
| 5,165,292 | 11/1992 | Prohaska | 210/198.2 |
| 5,376,252 | 12/1994 | Ekstrom | 210/198.2 |
| 5,378,583 | 1/1995 | Guckel et al. | 430/325 |
| 5,500,071 | 3/1996 | Kaltenbach | 210/198.2 |
| 5,544,276 | 8/1996 | Loux | 96/102 |
| 5,549,819 | 8/1996 | Nickelson | 210/198.2 |
| 5,571,410 | 11/1996 | Swedberg | 210/198.2 |
| 5,580,523 | 12/1996 | Bard | 210/198.2 |
| 5,611,846 | 3/1997 | Overton et al. | 96/102 |
| 5,641,400 | 6/1997 | Kaltenbach | 210/198.2 |
| 5,646,048 | 7/1997 | Templin | 210/198.2 |
| 5,658,413 | 8/1997 | Kaltenbach | 210/198.2 |
| 5,792,943 | 8/1998 | Craig | 210/198.2 |

OTHER PUBLICATIONS

Preparative Capillary Chromatography—A Proposal, pp. 6–7, Journal of High Resolution Chromatography & Chromatography Communications, Jan. 1988.

The Height Equivalent To A Theoretical Plate of Retentionless Rectangular Tubes, pp. 1–8, Journal of Chromatography, 1981.

*Primary Examiner*—Ernest G. Therkorn
*Attorney, Agent, or Firm*—Kean, Miller, Hawthorne, D'Armond, McCowan & Jarman; Russel O. Primeaux

[57] ABSTRACT

A novel chromatograph is provided. The chromatograph includes an analytical column which is a channel with a rectangular cross-section. Integrated with the chromatograph are a sample collection channel and a restriction channel. The column, sample collection channel, and restriction are all part of a single unitary microstructure. The microstructure is manufactured by irradiating and etching a material subject to synchronized x-ray radiation. The device will either be made of the actual etched material, or the etched material will be used as a mold or model to fabricate the chromatograph. A method of using the device is also disclosed.

12 Claims, 5 Drawing Sheets

MICROSTRUCTURE CHROMATOGRAPH WITH RECTANGULAR COLUMN

BACKGROUND OF THE INVENTION

1. Field of the Invention

This invention relates, generally, to analyses using devices for liquid and gas chromatography, and particularly to very small chromatographic devices and analyses.

2. Prior Art

Chromatography is the group of separation techniques in which a mobile phase (either a gas or liquid) is flowed over a stationary phase (either liquid or solid). As the mobile phase moves past the stationary phase, repeated adsorption and desorption, or partitioning, of the solute occurs at the rate determined chiefly by the solute's ratio of distribution between the two phases (partition ratio, K).

A gas chromatograph (GC) is an analytical instrument which uses the principle discussed above to separate and identify the solute compounds as a gas that are present in a sample. Typical GCs will include an analytical column with a gas carrier source and sample inlet at one end and a detector at the other end. The device which obtains the sample, and which extracts the analytes from the sample, can either be integrated with the GC or be a separate device.

Most GC's will include a means of heating the column as the analytes are moved through the analytical column by the carrier gas. In conventional GC's the heating is achieved by enclosing the entire column within an oven, and the oven GC's are very bulky devices. Some advances have been made in the field to allow for smaller gas chromatographs. For example, newer means for heating the column have been discovered. U.S. Pat. No. 5,611,846 to Overton et al discloses a GC which uses electrically resistive heater wire placed adjacent to the analytical column for heating of the column. This configuration allows for a device of less bulk than conventional oven GCs. However, even the device of the '846 patent is not built to such a miniature scale so as to be easily adaptable to personal sensor applications.

The need is clear and urgent for speciating chemical sensors that respond to the concentration of specific chemicals in complex mixtures. Conventional GCs and gas chromatograph/mass spectrometers (GCMS) have the capability to respond to the concentration of specific substances in complex mixtures but are certainly not "sensors" in terms of their size and functionality. If the speciating capability of certain conventional GC instruments could be fitted into the small size and operational functionality of common sensors, this development would result in a true speciated chemical sensor.

In this application, the name "GC sensor" will be used to describe this new type of analytical instrument that uses gas chromatographic technology for its speciating analytical capability. If GCs could be sufficiently miniaturized to function as GC sensors, multiple GC sensor modules could be placed in an array within a single instrument. Each GC sensor in this array could be designed for the performance of separate analytical functions. Redundant and simultaneous testing could be done, or each GC sensor could be designed to test for a specific compound. Currently, such selectivity is only achievable with large and expensive "hyphenated" analytical instruments such as GCMS.

Selectivity is extremely vital in GC in applications such as bomb and chemical warfare agent detection. Multiple GC sensor modules can also be tailored to provide analyses of compounds with widely different chemical characteristics. For example, one sensor module could be fitted with a molecular sieve column for separation of the permanent gases such as hydrogen, nitrogen and oxygen while another sensor module could be fitted with a column for the separation of BTEX components, or hydrocarbons in the range C14 to C25.

In many GC applications one desires to perform testing which requires two or more GCs. If one wants to test across an extremely broad dynamic range one must use multiple instruments, with their attendant bulk. Miniature GC devices would allow such testing to be done in a field environment. Miniaturization also decrease the power requirements of conventional GCs.

Conventional GCs are currently designed to handle a very wide variety of analytical applications. The disadvantage of this design philosophy is that each instrument has much unused capability in any given application. Unused capability in analytical instruments translates into extra cost, size, power consumption, and complexity. There is a need for small, rugged, and relative inexpensive analyzers that have satisfactory performance within certain applications but, in general, cannot be applied to a wide variety of other applications. Analytical instruments using GC sensor modules need not have all the analytical capability of laboratory devices, but if needed the instruments could be designed with such capability.

Outside of the field of gas chromatography, many advances have been made in the miniaturization of mechanical as well as electrical devices. One technique for the manufacture of very small devices is the use of synchronous x-ray radiation, such as that available from a synchrotron, to irradiate material which is sensitive to the radiation. The material can then be etched, leaving very fine and intricate structures.

The remaining structure can itself be the actual desired structure, or it can be used as a mold for the electrodeposition of metal. Again, the deposited metal structure can be the desired structure, or it too can serve as a mold for other materials. The resulting device, whether created from a mold or directly from the etching process, is extremely small and has extremely high resolution. It also can have extremely tall, accurate, and sharp vertical structures, and for this characteristic the devices are referred to herein as high aspect ratio microstructures (HARMs). HARMs have been made in various configurations such as valves, switches and heat exchanger surfaces. However, the inventor is unaware of any adaptation of HARMs to gas chromatography.

Many applications of GC analysis, spanning a wide variety of fields, require decisions to be made based on the concentration of specific chemical compounds in complex mixtures. This type of analysis, analysis that provides data on concentrations of specific chemical species, is called compound-specific analysis. Compound specific analysis can be used in environmental, medical, industrial, transportation, energy, service/facilities, educational, military, and other applications.

Specific examples of applications for a device which incorporates one or more GC sensors capable of compound-specific analysis could include:
- an airport security guard using the device to check for explosives;
- police using the device to search a cruise ship following a bomb treat;
- using the device to monitor a subway station for chemical nerve agents following reports of a strange odor in the station;

emergency officials using several devices located throughout a city to detect chemical emissions during a fire at a nearby chemical manufacturing plant, and order evacuations as appropriate;

a customs inspector using the device to detect contamination of foodstuffs by an illegal pesticide;

a petrochemical plant increasing its efficiency and product quality by monitoring process streams with many devices to rapidly detect unwanted deviations from operational and product specifications;

a medical professional using the device to perform rapid, inexpensive, non-invasive screening for metabolic diseases; and a commodity inspector using the device to detect the freshness of raw product.

Current "sniffing" technology is not technology at all, but instead relies on dogs in serious situations involving drugs and explosives. There are myriad other applications which will arise given our technology driven society.

OBJECTS OF THE INVENTION

It is an object of the present invention to provide a GC analytical device which is small enough for use as a handheld device.

Another object of the present invention is to provide a GC-based analytical device which is smaller and lighter than current GCs.

Another object of the present invention is to provide a CG sensor which is adaptable for multiple GC sensors in arrayed configurations.

Another object of the present invention is to provide a sensor type device which is capable of compound-specific analysis.

Another object of the present invention is to provide a GC device which can be manufactured using HARM manufacturing techniques.

Another object of the present invention is to provide a GC sensor which is adaptable to temperature programming techniques and which has the ability to extract analytes from samples.

SUMMARY OF THE INVENTION

A device known as the GC sensor is provided for chromatographic analysis. Conventional GC devices use a traditional tubular analytical column with a circular cross-section. Instead the GC sensor device has a column which has a rectangular cross-section. The column is part of a unitary microstructure which contains the column as well as a sample collection section and a restrictor. Optionally, a detector can be included in the unitary microstructure. This unitary microstructure is manufactured using what are known in the art as LIGA micromachining techniques or other techniques which will produce high aspect ratio microstructures (HARMs). A planar section of material which is susceptible to radiation and etching is irradiated and then etched in solution. The irradiation pattern produces very tall and very narrow channels in the material. Once a top is sealed onto the material the four sides of the column are formed.

Rather than serve as the end product, the material subject to etching can form a mold or model and the ultimate product can be made of metal, quartz, or some other material. Two or more of the devices can be set in an array. With each device designed to detect specific compounds, the array can be tailored for specific application.

A feature of the novel GC device is that it uses less power than a conventionally configured GC.

An additional feature of the novel GC device is that it can be completely automated.

An additional feature of the invention is that several of the GC sensors can be integrated into a sensor array.

An additional feature of the invention is that its small size allows for it to be carried or worn by an individual.

These and other objects, advantages, and features of this invention will be apparent from the following descriptions of the invention.

DETAILED DESCRIPTION OF THE PREFERRED EMBODIMENTS

Figure 1:
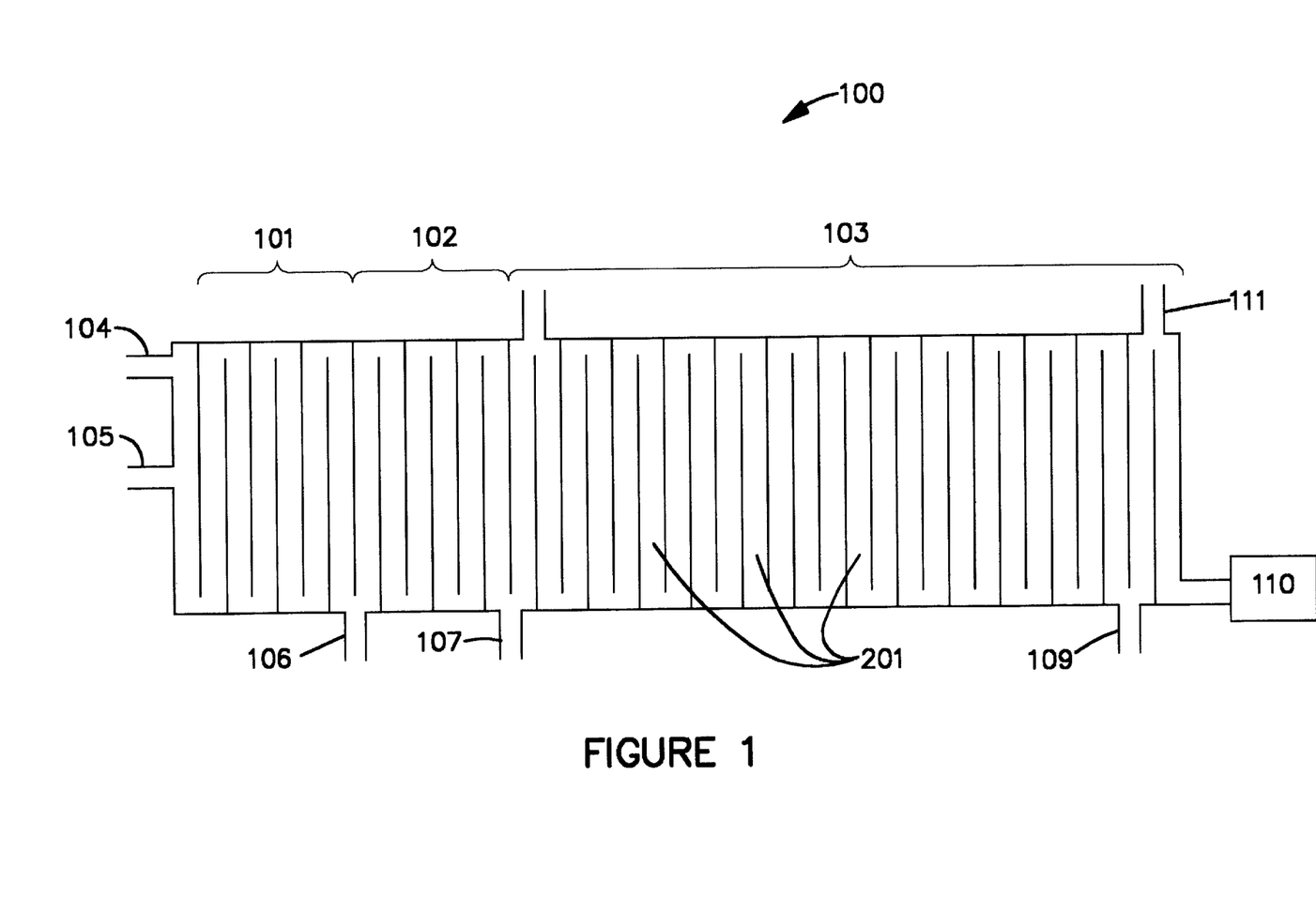
FIG. 1 is a schematic view of the parallel plate embodiment of the invention.

With reference to FIG. 1, an embodiment of the GC sensor will now be described. GC sensor 100 will include three general sections indicated by brackets and identified as sample section 101, restrictor 102, and analytical column 103. Sample section 101 will include sample section carrier inlet 104 and sample inlet 105. Although in the embodiment shown sample inlet 105 and sample section carrier inlet 104 are shown entering sample section 101 at different points, they could share the same opening. Restrictor 102 will include restrictor inlet 106 and restrictor carrier inlet 107.

Analytical column 103 includes first pressure sensor 108, second pressure sensor 109, detector 110, and make-up gas port 111. Some detectors require more gas flow than is used in the column. Make up gas port 111 provides this extra flow when needed. As shown in FIG. 1, sample section 101, restrictor 102, and analytical column 103 can all be part of a single layer microstructure sensor 100. The section of analytical column nearest detector 110 is the detector end; the section nearest restrictor inlet 106 is the intake end.

In one preferred embodiment, the entire parallel plate channel structure 200, shown schematically in FIG. 1, has overall dimensions of 4 cm wide×10 cm. long×0.5 cm. high, resulting in a channel which is 2000 microns high, 50 microns wide and 10 meters long. Restrictor 102 and sample section 101 are fluidly connected to analytical column 103 and have similar cross-sectional dimensions but are not as long as analytical column 103.

Preferably the proportionate lengths of analytical column 103, restrictor 102, and sample section 101 are in the range of 70/15/15 to 70/20/10. These ranges are for an embodiment in which the channel is uniform throughout GC sensor 100. In other embodiments analytical column 103, restrictor 102, and sample section 101 can have different cross-sectional dimensions and the proportionate lengths can be varied.

Figure 2:
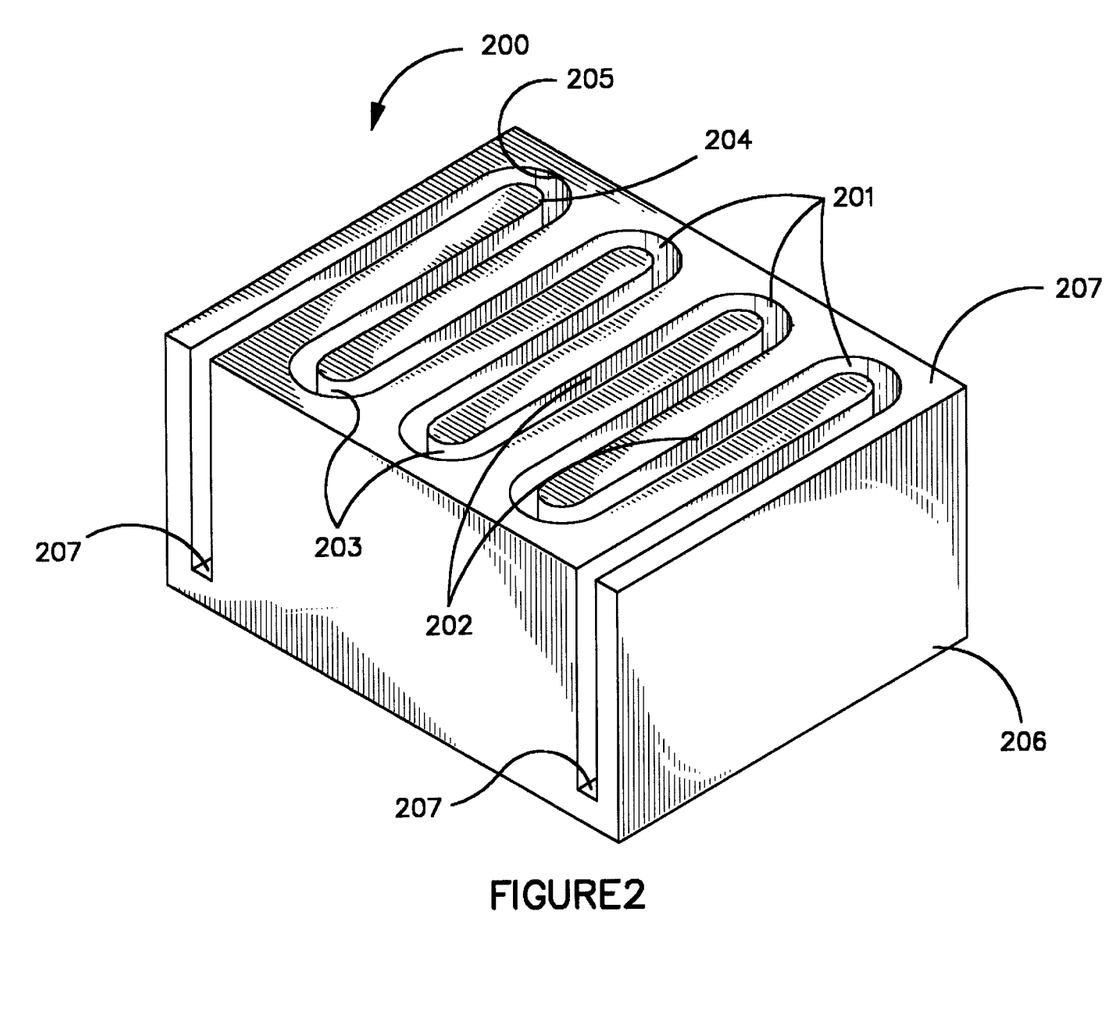
FIG. 2 is a perspective view of the parallel plate channel structure. The device is shown without a top plate.

FIG. 2 depicts one perspective view of a parallel plate channel structure 200 with parallel plate channel 201. This type of parallel plate structure is used for all three sections of GC sensor 100 depicted in the schematic view in FIG. 1. Parallel plate channel 201 will include straight channel portions 202 and curved channel portions 203. Each curved channel portion 203 will have inner radius 204 and outer radius 205. In a preferred embodiment inner radius 204 and outer radius 205 of each curved channel will be centered about the same point. This feature of the concentric turn radii, together with straight channel portions 202 being connected at alternating ends, will promote laminar flow though parallel plate channels 201.

Figure 3:
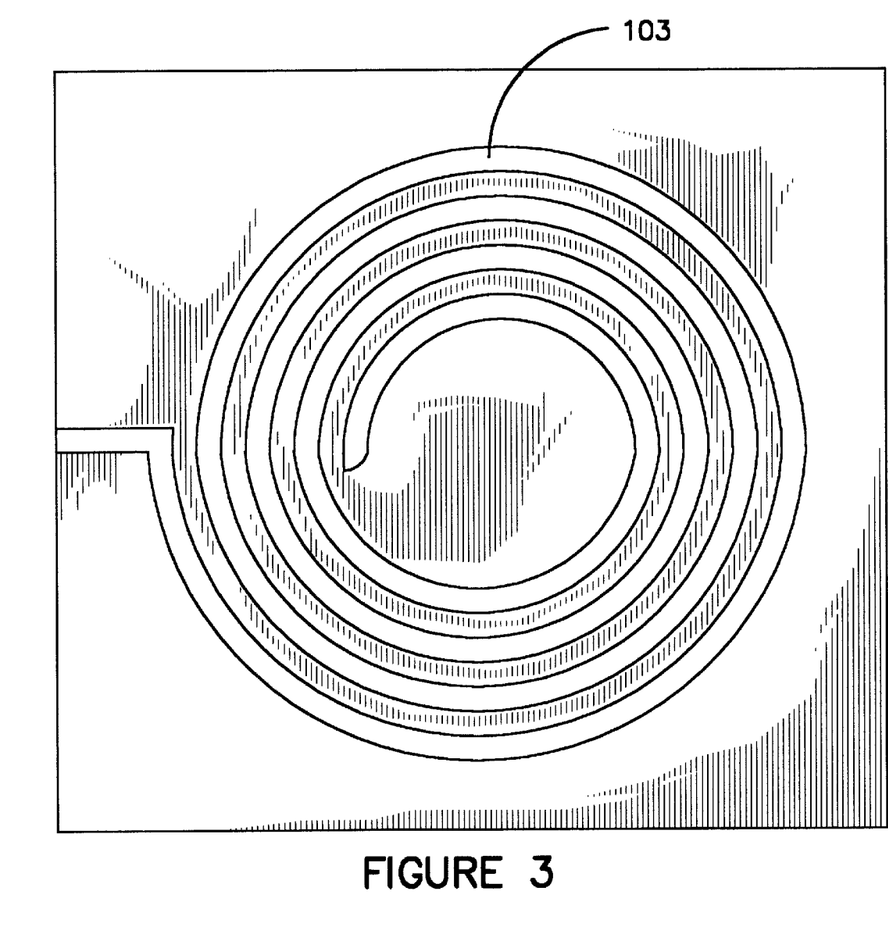
FIG. 3 is a top view of a spiral channel structure. The device is shown without a top plate.

In another embodiment, sample section 101, restrictor 102, and analytical column section 103 can be constructed using spiral channel structure 300. A top view of spiral structure 300 and spiral column 301 is shown in FIG. 3. Because one cannot make lateral connections to inner sections of spiral column 301 without crossing outer sections of the same spiral column 301, connections to spiral column 301, such as those for sample inlet 106 and sample vent 105, are made either though the top (not shown) or bottom of spiral channel structure 300. Although such top and bottom connections could also be made for parallel plate channel 201 shown in FIG. 2, such connections are only required for the inner sections of spiral column 301.

The methods by which the microstructure devices described herein are manufactured will now be described. Although these methods are discussed so as to fully enable the invention, it is the intention of the inventor that the scope of the invention includes other methods of manufacture, including those discovered in the future, so long as the methods produce the devices described and claimed herein.

In order to achieve the extremely small dimensions necessary for the GC sensor, micro-manufacturing techniques must be used. For the accuracy and size required for gas chromatography, it is believed that the preferred methods of manufacture for the GC sensor described herein will be the so-called LIGA method or other HARM manufacturing methods.

As discussed above, in GC the analytes are separated into their various compounds as they elute from the analytical column. If the analytical column has a very large cross-section the various compounds will elute from the column in wide bands. Wide bands are undesirable because there is a greater chance that the wide band of one compound will overlap with the wide band of another compound, thereby causing co-elution of each compound from the analytical column.

Conversely, if the cross-section of the column is made smaller the specific compounds in the analyte will separate and elute from the analytical column in very narrow bands. These narrow bands allow for more complete separations by the column. Therefore it is desirable to achieve cross-sections as small as possible. These small cross-sections are best achieved by microstructure manufacturing techniques.

Conventional gas chromatographic capillary columns are typically small open tubes with internal diameters of 270 to 530 microns and lengths of 10 to 30 meters. The inside walls of these columns are coated with a thin even layer of organic polymer, the GC liquid phase, to a thickness of typically less than one micron. As the diameter of the columns is reduced and the length increased, peak widths become more narrow following predictable chromatographic theory. This narrowing of peak widths, resulting in higher resolution between closely eluting compounds, is a beneficial result of using very narrow column dimensions.

Unfortunately, as the column diameter is decreased, the benefits of increased resolution are somewhat offset by the need for higher carrier gas pressures and lower amounts of sample that can be injected before the column overloads. In the current invention the analytical column will be a rectangular structure with high aspect ratio dimensions (i.e., very narrow and tall, or very wide and short) instead of the conventional cylindrical tube used in past GC technology. Although others have attempted to design rectangular cross-section columns in the past, the devices have been hard to reproduce accurately and easily.

The practical challenges in manufacturing rectangular tubing have prevented widespread development and acceptance of GCs with columns having a rectangular cross-section. The use of LIGA and other HARM manufacturing techniques not only allows the fabrication of such columns, it also allows one to make these columns with very narrow dimensions for extremely high resolution. Such small size columns possess, to an extreme degree, the positive attributes discussed above without the over-pressure and overload characteristics of conventional narrow band tubular columns. HARM techniques also allow for the manufacture of such devices which are mechanically rugged and accurately reproducible.

Parallel plate or spiral columns produced using LIGA or HARM techniques offer a means for realizing the high resolution capabilities of microbore GC columns without the usual sacrifice in sample capacity and dynamic range. For example, rectangular parallel plate columns, having cross-sections equivalent to the internal diameters of narrow bore tubular columns, can have an order of magnitude more chromatographic surface area, and thus sample capacity, than conventional capillary columns. The conventional gas chromatography model predicts a decrease in resolution with an increase in column diameter. This resolution loss follows from the assumption of laminar flow in the column.

Under laminar flow conditions, the carrier gas velocity across the column cross section is described by a parabolic function that varies from a maximum in the center of the column to zero at the column wall. This means that analyte molecules distributed homogeneously across the columns cross section are carried down the column at different velocities depending on whether they are situated near the center or near the sides of the column. The result of this flow velocity variation is an increase in the width of the eluting analyte band.

Because in the present invention the columns are very narrow the flow velocity variation is decreased. Yet because the columns are also very tall a larger amount of sample can be analyzed. In the rectangular cross-section column of the current invention, as an analyte molecule elutes from the vertical sidewall the molecule moves only away from the vertical sidewall and towards the detector end of the column. The analyte molecules exhibit little or no movement in the up and down direction, the direction parallel to the vertical sidewalls and perpendicular to the top and bottom walls of the column.

LIGA, a term derived from the German words for the process, involves irradiation of a photoresist substrate material, such as polymethyl methacrylate (PMMA). The substrate is chosen so that after being exposed to radiation, those irradiated portions can be etched away with an appropriate etching solutions. LIGA techniques are discussed generally in W. Ehrfeld, et al, "LIGA Process: Sensor Construction Techniques Via X-Ray Lithography," Technical Digest IEEE Solid State Sensor and Actuator Workshop, 1988, pp. 1–4.

Selective portions of the substrate will be irradiated in a pattern which is the desired shape of the structures to be created, or a negative of those structures. The preferred type of radiation is synchronized x-ray photons generated by a synchrotron. Synchrotron radiation is preferable because its strength and frequency can be accurately regulated to control the depth to which the substrate is to be etched.

Several materials could be used for the GC sensor. One could use the LIGA techniques to etch a substrate layer which would serve as a negative for the ultimate shape of the GC sensor. This substrate could then be electroplated with a metal, such as nickel, to create GC sensor 100. The surfaces of the interior channels, such as parallel plate channel 201 or spiral channel 301, are deactivated using electropolishing or surface bonding techniques. The metal structure can also be used a model for the creation of plastic or ceramic molds, and these molds could be used to create additional metal GC sensors. If the electroplating process is employed to create metal structures the substrate layer must include below it a metal plate onto which the metals may be electroplated.

In another embodiment, one could use LIGA techniques to etch a substrate which is as a positive of the GC sensor. This substrate would then be electroplated with a metal and the resulting metal structure would be a negative. This metal negative could be used as a mold to create final structures. This could be accomplished by filling the metal negative with plastic or ceramic. In a particularly preferred embodiment, the GC sensor would be constructed of quartz or a rigid solgel silica material. Preferably, these non-metallic GC sensors will be coated with a thin metal layer so that they are better conductors of heat.

A process for the manufacture for parallel plate channel structure 200 will now be described. The process will discuss an embodiment of parallel plate channel structure 200 which is composed of quartz coated with metal. The process begins with an initial substrate of material susceptible to X-rays and etching (e.g. PMMA or other photoresist material). Selective portions of the PMMA are exposed to x-ray photon radiation, leaving a substrate which has the general appearance of parallel plate channel structure 200. The selective irradiation of the PMMA is performed by beam direction techniques or by placing a patterned mask over the PMMA. The strength and wavelength of the x-ray photons will be controlled so that the radiation, and subsequent etching, will remove almost all of the PMMA in parallel plate channels 201 but will not remove bottom layer 206. The top surface of bottom layer 206 serves as channel bottom surface 207 of parallel plate channel 201.

In an alternative embodiment one could also begin with a dual layer material. Bottom layer 206 could be made of metal and the remainder of the substrate would be constructed of a material susceptible to radiation and etching (e.g. PMMA) which was bonded to the metal. The dual layer material could then be irradiated and etched to create a structure with the appearance of parallel plate channel structure 200. Additional metal may then be electroplated onto this exposed metal surface, filling parallel plate channel 201 up to a desired thickness.

The structure is exposed to radiation and etched again, and only the metal bottom layer 206 and the electroplated metal structures remain. The resulting metal structure is a negative of parallel plate channel structure 200. This negative is filled with quartz to create a parallel plate channel structure 200 made of quartz. Parallel plate channel 201 is then coated with a thin metal layer.

For all of the methods and materials discussed above the resulting structure will have the general appearance of parallel plate channel structure 200. Parallel plate channel structure 200 will be sealed on the top with a top plate (not shown). For a single GC sensor 100 the top plate will be constructed of a material which can be bonded to, and which is the same as or compatible with, the material in parallel plate structure 200. The top plate could be a simple plate, a manifold with ports and openings which make up the various connections to GC sensor 100 shown in FIG. 1, a temperature control means, or the bottom plate of another GC sensor 100 if the sensors are stacked in an array.

Figure 4:
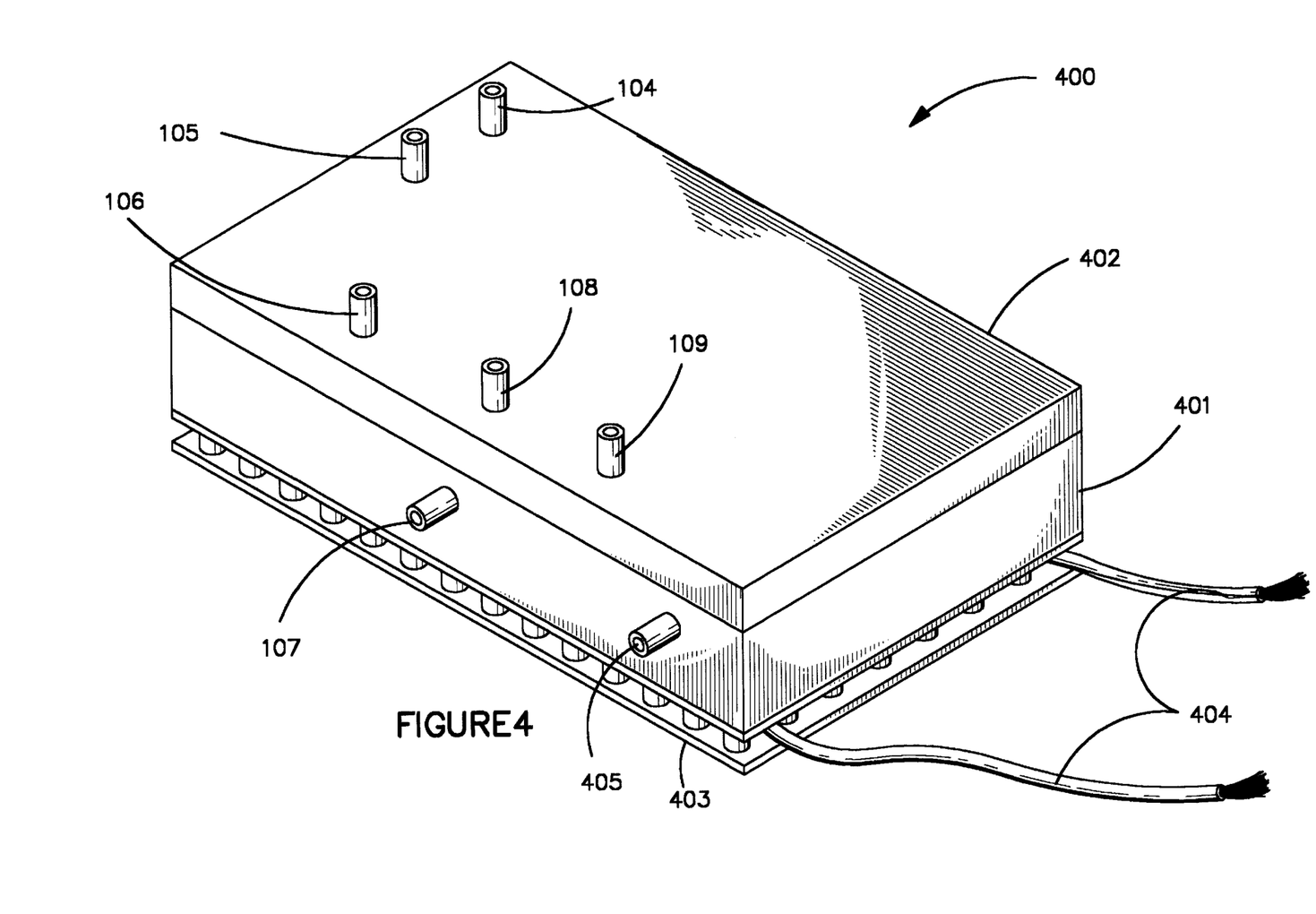
FIG. 4 depicts a GC sensor in an embodiment which includes a manifold as top plate and a Peltier cooler as a bottom plate.

FIG. 4 shows complete GC sensor 400 which includes top plate 402 and channel structure 401. In the embodiment of FIG. 4 GC sensor 400 will also include temperature control means 403. In one particularly preferred embodiment temperature control means 403 is a device is known in the art as a Peltier cooler, which can be used for the temperature programming techniques which will be employed with GC sensor 400. One could also employ an electrically resistive plate as temperature control means 403.

In one preferred embodiment channel structure 401 will be made of nickel, which conducts heat very effectively. In this embodiment electrically resistive heating of GC sensor 400 itself can be used, eliminating the need for temperature control means 403. Because nickel has excellent thermal conduction properties, temperatures will be homogenous across relatively thin (0.4 mm) sections of nickel which make up channel structure 401. Those skilled in the art may use other metals and other materials which are inert to the GC process and which can be heated homogeneously. The miniaturization of the chromatograph and the heating of only those components which must be heated allows for efficient power usage not possible with conventional GCs.

In another embodiment top plate 402 is an electrically resistive plate used in combination with a Peltier cooler as temperature control means 403. Each such device can be connected to a temperature programming microprocessor (not shown) via electrical leads 404. Such a combination will provide for the use of precise temperature programming techniques with GC sensor 400.

In another preferred embodiment, more than one electrical circuit can be made on a parallel plate structure 200 or on an adjacent plate. In this embodiment discreet portions of GC sensor 100 can be heated to one temperature while others are left at ambient temperature or heated to a different temperature.

In the embodiment depicted in FIG. 4 top plate 402 is a manifold bonded onto channel structure 401. The manifold includes the ports, valves, and connections shown in a schematic view in FIG. 1. Manifold 402 includes detector port 405, sample section carrier inlet 104, sample inlet 105, restrictor inlet 106, restrictor carrier inlet 107, first pressure sensor 108, and second pressure sensor 109.

Figure 5A:
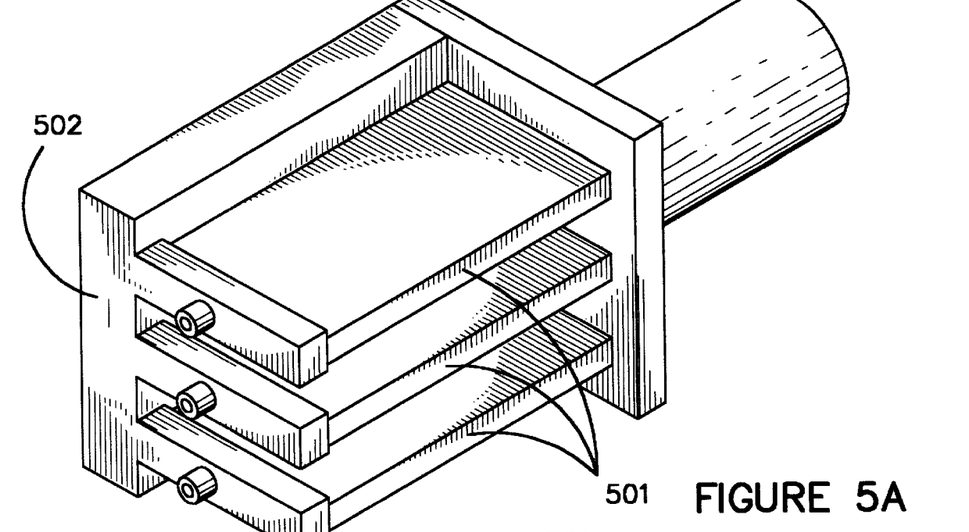
FIGS. 5A–5C are plan views of an instrument which includes multiple GC sensors set in an array.
Figure 5B:
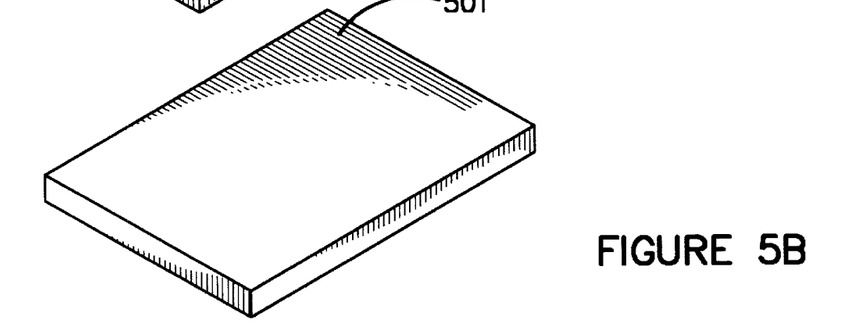
Figure 5C:
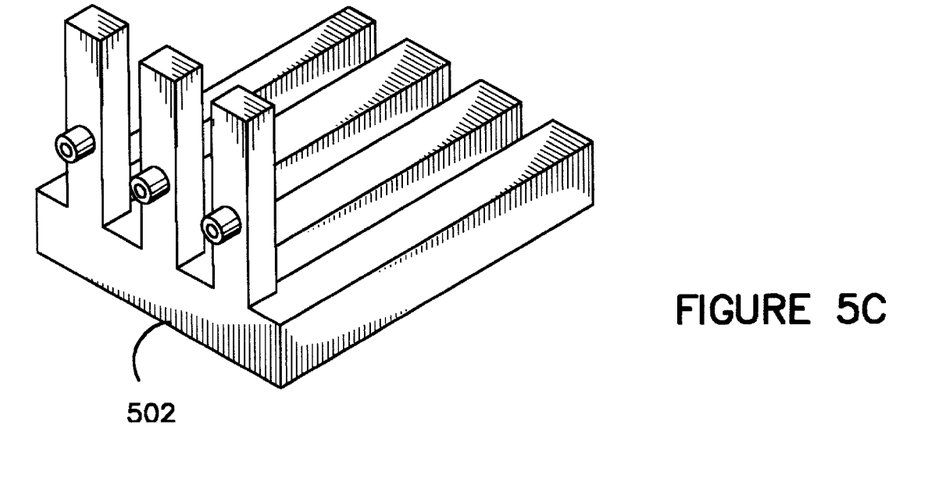

FIGS. 5A through 5B depict sensor array 500 which will include one or more GC sensors 501. GC sensors 501 can include the elements shown in FIG. 4; however for purposes of illustration in GC sensors 501 in FIG. 5A through 5B are shown in plan view only. Sensor array 500 will include array housing 502. In a preferred embodiment each GC sensor 501 can be designed to check for specific compounds. This ability to speciate each GC sensor 100 may be achieved by variances in column dimensions, column coating, temperature programming, type of detector, and other design choices.

Although the embodiment of sensor array 500 depicted in FIGS. 5A–5B has three GC sensors 501, one skilled in the art can design sensor array 500 so as to include any number of GC sensors. Additionally, because each GC sensor 501 is modular, specific GC sensors can be interchanged on sensor array 500 for particular applications.

The inventor believes the essence of the invention is the use of the LIGA or HARM techniques, which allow for the creation of high aspect microstructures not achievable with other manufacturing techniques, to produce a gas chromatograph which is extremely small, yet accurately and reliably reproducible; the devices produced from such a method; and the uses of that device.

With reference to FIG. 1 the operation of GC sensor 100 will now be described. Column 103 will be coated with bonded and cross-linked GC liquid phase. Sample section 101 and restrictor 102 can be uncoated. Carrier gas flow is maintained through the column by applying the appropriate carrier gas pressure at sample section carrier inlet 104. The sample to be tested is drawn into the sample loop while the instrument is at ambient temperature.

The sample may be flowed into sample section 101 by flowing sample gas (not shown) into sample section inlet 105 at a higher pressure that the pressure at restrictor inlet 106. Preferably, this pressure differential is created by placing a vacuum at restrictor inlet 106. These settings will cause the sample to be drawn into sample section inlet 105, which includes a check valve. This method of sample intake is not the only method available; the sample could be drawn or pumped into sample section 101 in many ways using different pressure differentials at the various ports of sample section 101.

As the sample is flowed into sample section 101, semivolatile analytes are trapped on the portion of sample section 101 nearest sample inlet 105 while volatile analytes fill the remaining void space of sample section 101. Alternatively, one can place a vacuum at sample section inlet 105 and draw the sample gas in through restrictor inlet 106, in which case the semivolatile analytes are trapped on the portion of sample section 101 nearest restrictor inlet 106.

In order to inject the analytes into column 103, restrictor carrier inlet 107 is closed and carrier gas is flowed into sample section carrier inlet 104. The amount of analytes injected will be determined by the length of time restrictor carrier inlet 107 is closed and sample section carrier inlet 104 is open as well as the pressure differential between restrictor carrier inlet 107 and sample section carrier inlet 104. This time can be on the order of 100 milliseconds and the pressure differential may be 15 to 25 psig.

After the desired quantity of analytes have been injected into column 103, restrictor carrier inlet 107 is re-opened and the temperature in column 103 is ramped from initial to final temperature at rates of 1 to 20 degrees C. per second. If semivolatile analytes are being analyzed, sample section carrier inlet 104 is reopened during temperature programming but after the volatile components have been injected or cleansed from the loop. As the temperature of GC sensor 100 is raised, semivolatile analytes move from sample section 101, through uncoated restrictor 102, and onto coated column 103 for separation during temperature programming. Eluting compounds are detected with detector 110. It will be obvious to those skilled in the art to use flame or photoionization detection, thermal conductivity detection, or any of several known methods to perform the detection function on the eluting analytes as they exit column 103.

There are of course other alternate embodiments which are obvious from the foregoing descriptions of the invention, which are intended to be included within the scope of the invention, as defined by the following claims.

I claim:
1. A GC sensor comprising an analytical column with an intake end and a detector end, said column having a substantially rectangular cross-section and said column being formed by a series of parallel passages connected at alternating ends in a substantially planar microstructure.

2. The GC sensor in claim 1 wherein said height of said cross-section is equal to or greater than approximately three times said width.

3. The GC sensor in claim 1 wherein:
 (a) said column further comprises an inner surface;
 (b) a liquid phase is disposed along said inner surface; and
 (c) the column width and height are selected such that as analytes are moved through said column molecules of said analyte will elute and exhibit relatively no movement in the direction parallel to a line along which said height is measured, but said molecules will exhibit substantially laminar flow as said molecules travel toward said detector end.

4. The device in claim 3 further comprising:
 (a) a sample section having a sample section carrier inlet and a sample inlet;
 (b) a restrictor fluidly connected between said sample section and said intake end of said column;
 (c) said sample section, said restrictor, and said column being part of a continuous channel contained in a channel structure having a bottom layer; and
 (d) a top plate bonded to said channel structure.

5. The device in claim 4 further comprising a temperature control means bonded to said bottom layer or said top plate of said channel structure.

6. The device in claim 5 wherein said temperature control means is a Peltier cooler or a resistance heater.

7. The device in claim 5 wherein said top plate further comprises a manifold.

8. The device in claim 7 wherein said temperature control means is a Peltier cooler or a resistance heater.

9. A device for chromatography comprising:
 (a) two or more GC sensors, each said sensor comprising:
  (i) an analytical column with an intake end, a detector end, an inner surface, and a liquid phase disposed along said inner surface, said column having a substantially rectangular cross-section;
  (ii) the column width and height for said rectangular cross-section being selected such that as analytes are moved through said column molecules of said analyte will elute and exhibit relatively no movement in the direction parallel to a line along which said height is measured, but said molecules will exhibit substantially laminar flow as said molecules travel toward said detector end;
  (iii) a sample section having a sample section carrier inlet and a sample inlet;
  (iv) a restrictor fluidly connected between said sample section and said intake end of said column;
  (v) said sample section, said restrictor, and said column being part of a continuous channel contained in a substantially planar channel structure having a bottom layer; and
  (vi) a top plate bonded to said channel structure;
 (b) an array housing to which said GC sensors are interchangeably attached; and
 (c) each said sensor being adapted to detect one or more specific compounds which the other sensors in said array housing are not adapted to detect.

10. A GC sensor comprising an analytical column with an intake end and a detector end, said column having a substantially rectangular cross-section, and said column being formed by a series of parallel passages connected at alternating ends in a substantially planar microstructure, said GC sensor being produced by the following method:
  a. providing a substrate of material susceptible to x-rays and etching;
  b. irradiating selected portions of said substrate material with synchronized x-ray radiation, said selected portions being chosen such that after etching a microstructure with three sides of said rectangular cross-section columns will be formed, the long sides of said rectangular cross-section being parallel to the path of said radiation;
  c. etching the material in an etching solution; and
  d. bonding a top to said material to form the fourth side of said rectangular cross-section of said column.

11. A GC sensor comprising an analytical column with an intake end and a detector end, said column having a substantially rectangular cross-section, said GC sensor being produced by the following method:
  a. providing a layer of metal bonded to a substrate of material susceptible to x-rays and etching;
  b. irradiating selected portions of said material with synchronized x-ray radiation, said selected portions being chosen such that after etching a microstructure with three sides of said rectangular cross-section columns will be formed, the long sides of said rectangular cross-section being parallel to the path of said radiation;
  c. etching the material in an etching solution;
  d. electroplating metal onto the metal plate so as to fill the portions which were etched away;
  d. filling the resulting metal structure with quartz such that a quartz microstructure with three sides of said rectangular cross-section column will be formed; and
  e. bonding a top to said quartz microstructure to form the fourth side of said rectangular cross-section of said column.

12. A GC sensor produced by the method in claim 11, comprising the additional step of coating the interior surfaces of said column with metal.

* * * * *